United States Patent [19]

Jilkén

[11] 4,316,146
[45] Feb. 16, 1982

[54] METHOD AND DEVICE FOR MEASURING AND DETECTING A CHANGE IN THE MECHANICAL STATE OF A BODY

[76] Inventor: Leif A. Jilkén, S-58252, Linköping, Sweden

[21] Appl. No.: 68,183

[22] Filed: Aug. 20, 1979

[30] Foreign Application Priority Data

Dec. 12, 1977 [SE] Sweden .............................. 7714053

[51] Int. Cl.³ ..................... G01B 7/24; G01R 33/18; G01R 33/12; G01N 27/72
[52] U.S. Cl. ..................................... 324/209; 324/232
[58] Field of Search ...................... 324/209, 232, 262; 73/779, 765, 794

[56] References Cited

U.S. PATENT DOCUMENTS 3,534,254 10/1970 Semienko et al. .................. 324/209

FOREIGN PATENT DOCUMENTS 489969 3/1974 U.S.S.R. ............................. 324/209

Primary Examiner—Gerard R. Strecker
Assistant Examiner—Walter E. Snow

Attorney, Agent, or Firm—Strimbeck, Davis & Soloway

[57] ABSTRACT

A method and device are described for measuring a change in the mechanical state aiming at detecting the disturbance the change in state has on a magnetic flux ($\phi$). This flux is brought to flow through at least a part of the body (1) under the influence of a driving magnetizing force ($H_0$).

In order to achieve an unambiguous measuring result the average length (l) of the magnetic circuit is kept constant and independent of the change in the mechanical state. The flux ($\phi$) consists partly of a main flux ($\phi_0$) having a definite direction and being of such a magnitude that the magnetic properties of the body depart from the region of irreversibility and partly of an alternating, gradually vanishing flux ($\phi_v$) superimposed upon the main flux. The alternating flux must have such an initial magnitude that saturation is obtained in both directions of the alternating flux ($\phi_v$). After the vanishing of the alternating flux ($\phi_v$) the disturbance generated through the change in the mechanical state is indicated or registered as a voltage which is induced by the change in flux corresponding to the disturbance.

5 Claims, 7 Drawing Figures

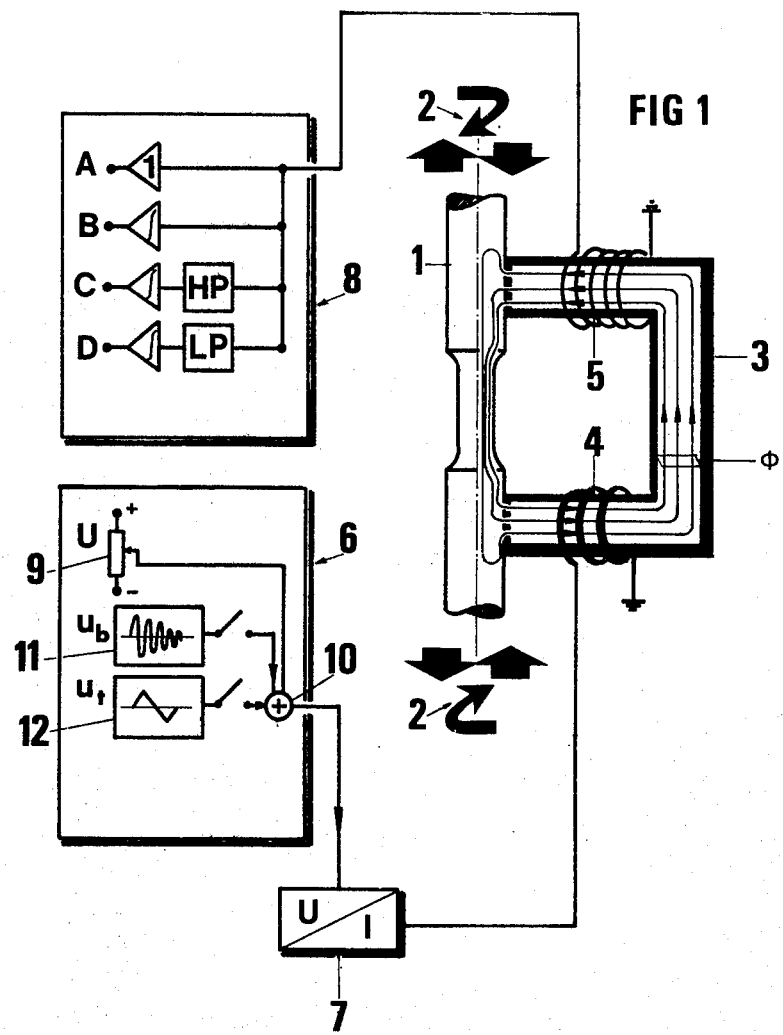

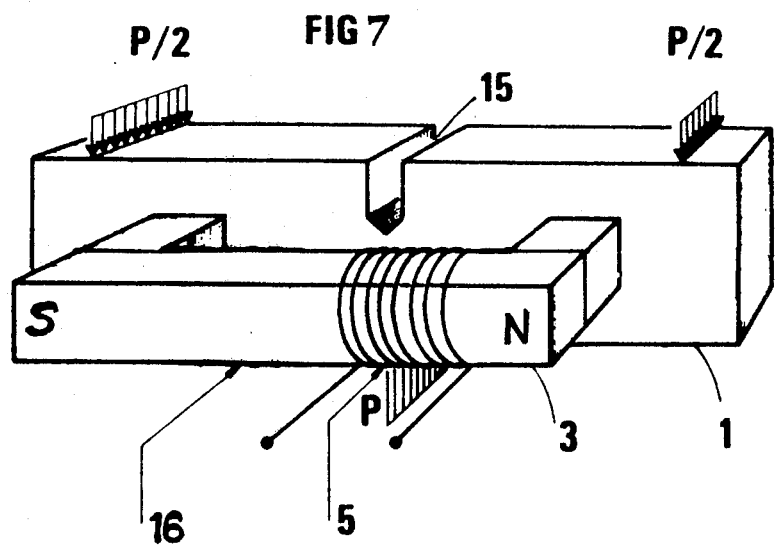

4,316,146

METHOD AND DEVICE FOR MEASURING AND DETECTING A CHANGE IN THE MECHANICAL STATE OF A BODY

TECHNICAL FIELD

The present invention relates to a method for measuring or detecting a change in the mechanical state such as a change in the mechanical load, yielding, initiation or propagation of cracks, separation within the material or vibration or a change in the mechanical state with respect to time in a body showing magnetostrictive effects, when, under the influence of a driving magnetic force (H), an associated magnetic flux is generated in at least a part of the body, on which flux the change in the mechanical state via the magnetization (M) of the body acts a measurable or detectable disturbance. The invention relates also to a device for carrying out the method.

BACKGROUND ART

Ever since Joule for the first time demonstrated the magnetostriction in 1842 and Villari the inverse phenomenon in 1865, the so called Villari effect, many measuring devices and methods have been suggested which have utilized the coupling between the magnetic flux and the change in the mechanical state. Common to all known such measuring devices and methods is that the average length of the magnetic circuit is allowed to vary with the change in the mechanical state. As is known, the magnetizing force is inversely proportional to this average length. Since the magnetization apart from the change in the mechanical state as well as variations in the average length of the magnetic circuit in these measuring devices.

The object of the present invention is to eliminate the above mentioned double dependence of the magnetization so that it only depends on the change in the mechanical state. This is achieved by keeping the magnetizing force ($H_0$) and the average length (l) of the magnetic circuit essentially constant and independent of the change in the mechanical state when measuring or detecting. The flux consists partly of a main flux ($\phi_0$) associated with the driving magnetic force ($H_0$) having a definite direction and being of such a magnitude that the magnetic properties of the body depart from the region of irreversibility, and partly of a superposed alternating flux ($\phi_v$) which gradually vanishes. This alternating flux must have such an initial magnitude that saturation is achieved in the two directions of the alternating flux ($\phi_v$) i.e. so that in a way known per se a point on the anhysteretic curve is reached when the alternating flux ($\phi_v$) has vanished. After the vanishing of the alternating flux ($\phi_v$), the disturbance which is generated by the change in the mechanical state, is registered as a voltage which in turn is induced by the change in the flux corresponding to disturbance.

DESCRIPTION OF THE FIGURES

The invention will be described in more detail in the following with reference to the appended drawing on which:

FIG. 1 shows schematically a device which is operated according to the invention when measuring a change in the mechanical state of a loaded body.

FIG. 7 shows a variation of FIG. 6.

DESCRIPTION OF A PREFERRED EMBODIMENT

Figure 3:
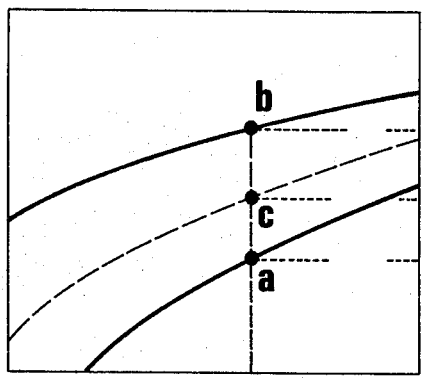
FIG. 3 is an enlarged part of FIG. 2 illustrating how, for a given value $H_0$ of the driving magnetizing force, the magnetic flux $\phi$ can assume a number of values, three of which are specially indicated in the figure.

In FIG. 1, the ferromagnetic body 1 is a test specimen, which is subjected to mechanical stress due to tension, compression or torsion, as is indicated by the arrows 2, acting individually or in combination as tension-torsion or compression-torsion. The stresses give rise to a change in the mechanical state of the specimen which can encompass elastic and plastic deformation, separation within the material, crack initiation, crack propagation and even fracture. It should be mentioned that a change in the mechanical state also can arise from thermal stresses. For measurements or detections of changes in the mechanical state in the body, it is provided with a number of yokes 3, one of which is shown in the figure, carrying a primary coil 4 and a secondary coil 5. By use of a voltage generator 6, connected via a voltage/current transformer 7 to the primary coil 4, a current is produced, which in turn generates the magnetizing force. This generates a flux through a magnetic circuit, which consists of the yoke 3 and a part of the specimen 1. The yoke shall be arranged in such a way in relation to the specimen that the magnetic circuit is essentially free from air gaps and so that the yoke is not affected by the stress. This can be achieved by letting the yoke 3 slide along the specimen 1. It is obvious that the coils may be placed anywhere along the magnetic circuit. The location of the coils is determined by practical considerations only. In order to achieve a symmetrical flux a number of parallel yokes should be used.

The change in the mechanical state acts, via the magnetizing of the body (in the sequel denoted by M), as a disturbance on the flux $\phi$, which is detected by the secondary coil 5 and indicated on an indicating unit 8 connected to the coil. According to the invention both the magnetizing force, in the following named $H_0$, and the average length l of the magnetic circuit shall be kept essentially constant and independent of the change in the mechanical state. As mentioned earlier the average length l is kept constant by allowing at least one of the two shanks of the yoke to slide along the specimen. The magnetizing force $H_0$ is kept constant by feeding the coil 4 with a constant direct current. This current is obtained by a divider of a voltage U by use of a potentiometer 9. Via a summation point 10 in the voltage generator 6 the voltage is applied to the converter 7, where the voltage is transformed to the constant current. As can be seen from FIG. 2 each value of the magnetizing force $H_0$ corresponds to a number of values of the flux $\phi$, two of which, a and b, have been marked on the hysteresis curve of the body and one, c, on the anhysteretic curve. Of said points, c is the one which corresponds to the value of the flux $\phi$ at which the specimen has reached its lowest electromagnetic energy for the given value $H_0$ of the driving magnetizing force.

Figure 4:
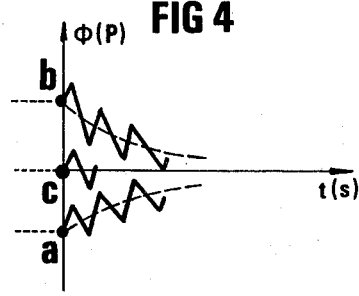
FIG. 4 shows with three curves how the magnetic flux in a body varies with time, when the body is subjected to triangular mechanical load pulses. The intermediate one of the curves is related to a measuring procedure according to the invention and the others to conventional measuring procedures.

If one, as in known measuring or indicating methods, starting from point a or b, tries to measure e.g. a saw-tooth shaped cyclically varying mechanical load acting on the specimen 1, the flux would vary as in illustrated by the two outer curves in FIG. 4, i.e. the flux is not equal in two corresponding points of two consecutive load cycles. The change in the mechanic state which is caused in the body by the load can thus not be unambiguously determined from the disturbance of the flux from the load.

According to the invention at the beginning of the measuring an alternating flux $\phi_v$, which gradually vanishes, is therefore superposed. This flux is produced by a generator 11 which supplies a voltage $u_b$ decreasing with time to the summation point 10 in the unit 6, FIG. 1. The object of the alternating flux $\phi_v$ is to bring the tested body to reach an initial state which is stable from an electromagnetic point of view. This will be the case if one starts from the anhysteretic curve. This curve relates, as contrasted to the hysteresis curve, the magnetization M unambiguously to the magnetizing force H. Furthermore, from a magnetic point of view, a departure must be made from the irreversible region of the body. In order to determine the value of the driving magnetizing force at which this happens, a triangular-shaped voltage $u_t$ is fed to the summation point 10 in the unit 6, FIG. 1. The hysteresis curve is then registered and from it a suitable value of the driving magnetizing force $H_0$ is selected beyond the above mentioned region. Hereafter the detection can be performed according to the invention.

Figure 2:
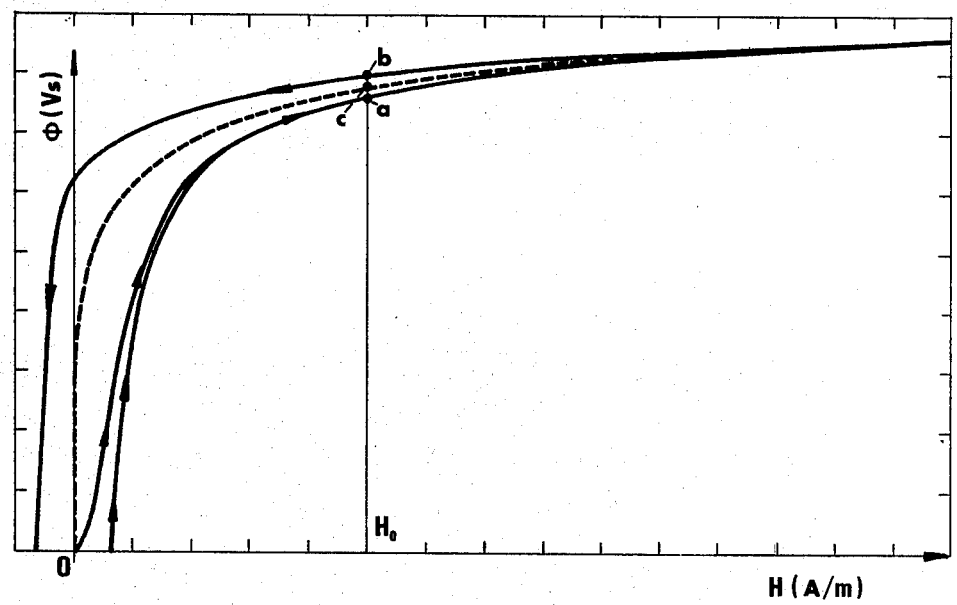
FIG. 2 shows by solid lines one half of the magnetizing curve for a ferromagnetic solid and by dashed lines the corresponding part of the anhysteretic curve of the body.

As has been mentioned, the point c in FIGS. 2 and 3 corresponds to the value of the flux $\phi$ at which the body assumes its lowest state of electromagnetic energy at the magnetizing force $H_0$. For other values of the magnetizing force there are of course corresponding values of the flux, which are to be found from the anhysteresis curve of the body. When according to the invention measuring the response of the flux to a mechanical load, i.e. the variation with time of the flux as a function of the load acting on the body, and starting from an electromagnetically stable, initial value, one finds that the flux is a unambiguous function of the load. When, for instance, the load has a saw-tooth shape the flux varies as illustrated by the intermediate curve in FIG. 4. For this curve the change flux is equal in corresponding points in two identical and consecutive load cycles. The mean value of the curve is time invariant during one or more cycles. This is obviously not the case for the two earlier described outer curves which illustrate measurements according to known methods. The mean value of these curves is not constant but tends toward the mean value of the intermediate curve. This could be explained by the supposition that energy is required for bringing the flux at points a and b to the same level as at c. This energy is taken from the change in the mechanical state which consequently cannot be stably reproduced in time through studies of the magnetic flux. The change in flux generated by the change in the mechanical state and detected by the measuring coil 5 as a voltage, can be used in a number of ways by the indicator unit 8 as illustrated in FIG. 1. A signal is obtained at output A proportional to this voltage as well as at output B corresponding to the time integral of the voltage. At exits C and D signals are obtained corresponding to the voltage after passage of a high-pass filter and a low-pass filter, respectively, and integration. Depending on the subsequent evaluation of the measurement the voltage can be treated in other ways e.g. being digitized.

Figure 5:
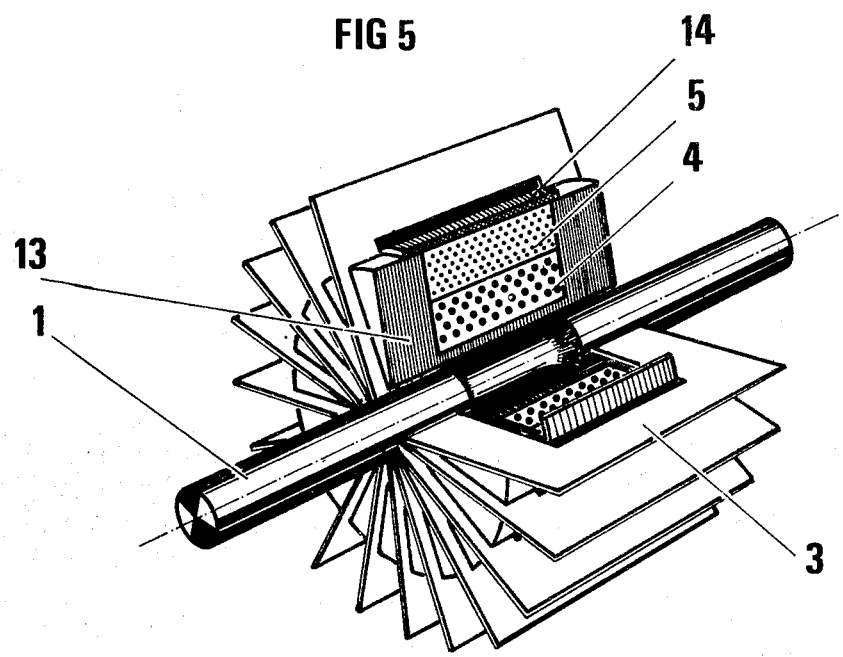
FIG. 5 shows in detail one embodiment of a device according to the invention and intended for measurements on a round specimen.
Figure 6:
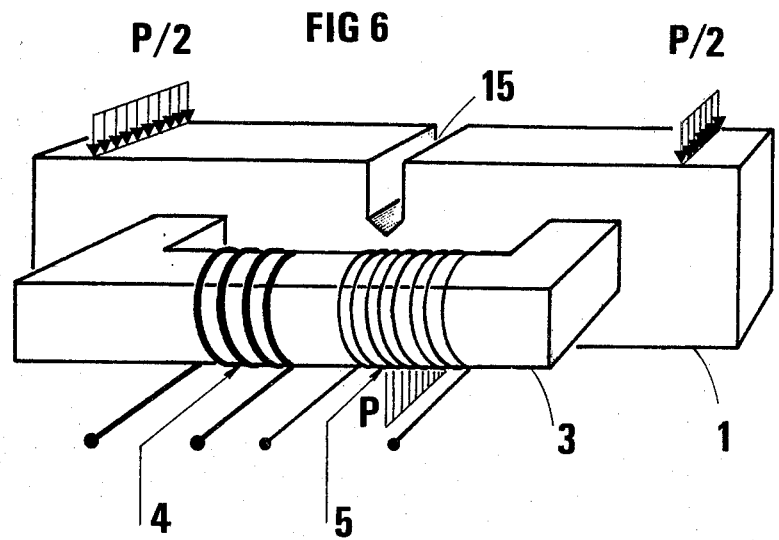
FIG. 6 shows in a projection a device to the invention for measuring on a notched threepoint bend specimen, which is subjected to bending forces.

In FIGS. 5 and 6 components having the same or corresponding functioning as those in FIG. 1 have been given the same reference numbers as in FIG. 1. In FIG. 5 the body 1 is a conventional cylindrical test specimen where the deformations occur mainly in the waisted section, assuming that its diameter is considerably smaller than the other parts of the specimen. The primary coil 4 and the secondary coil 5 are wound on a tube-shaped coil core 13 with end walls. The central hole of the coil core is of such a size as to allow an easy penetration of the body. The coils 4 and 5 are protected by a cover 14. The positioning of the coils 4, 5 was chosen to obtain as small a leakage and as homogeneous a flux as possible. To obtain a symmetric flux through the body 1 a number of yokes 3 have been placed symmetrically around the coil core. These are U-shaped plates intended to slide in radially arranged slits in the end walls of the coil core 13.

The body 1 can slide relatively free in the central hole of the coil core 13 which leads to a constant average length of the magnetic circuit independent of the applied mechanical loads. The yokes 3 are held in place during the measurement by magnetic forces between the yokes and the body. When measuring is not performed the yokes can be secured by e.g. elastic strings or hoops closing the yokes.

ALTERNATIVE EMBODIMENT

In FIG. 6 the body 1 is a conventional threepoint bend specimen having a rectangular cross section. In the center of the specimen is a notch 15. The primary and secondary coils 4 and 5 are placed on yokes 3, of which only one is shown in FIG. 6. The yokes are placed symmetrically with respect to the notch on the longitudinal sides adjoining the upper side.

During the measurement the specimen is loaded with forces as is showed by arrows in the figure so that the specimen is mainly subjected to bending stresses. The forces P/2 are applied from above symmetrically with respect to the notch 15 and the force P acts from below at the notch 15. According to the invention, the stress must not influence the average length of the flux. Hence, the yokes 3 are slidably arranged relative to the specimen. The measuring should be carried out as is described above in connection with FIG. 1.

It is obvious that the invention must not be considered to be limited to the embodiments described and is illustrated above. On the contrary the measuring method can, as is stated in the appended patent claims, be used in many measuring applications. With one or more yokes, provided with primary and secondary coils and applied to an arbitrary magnetizable body, e.g. a stay crutch, a beam, a rod or a plate acted upon by a load, the change in the mechanical state due to the load can be measured. The presumptions for this is that one starts from a point on the anhysteresis curve of the body and that the average length of the flux is not affected by the load.

The main magnetic flux has in the applications above been generated by use of one or more primary coils, but can, as is apparent from a special characteristic of the invention, also be produced by permanent magnets, as illustrated in FIG. 7 which is a variation of the embodiment of FIG. 6 in which the primary coil 4 has been replaced by permanent magnet 16. These are arranged in such a way that the main flux is constant.

For measurements of the flux, solutions other than the above described secondary coil are possible. For this purpose e.g. a so-called Hall element can be used.

I claim:

1. A method for measuring or detecting a change in the mechanical state such as a change in the mechanical load, yielding, crack initiation, crack propagation, separation within the material or vibration or the time derivative of the change in the mechanical state in a body showing magnetostrictive effects, when, under the influence of a driving magnetizing force (H) an associated magnetic flux is generated in at least a part of the body, on which flux the change in the mechanical state via the magnetization (M) acts as a measurable or detectable disturbance, characterized in that the driving magnetizing force ($H_O$) and the average length (l) of the magnetic circuit are kept essentially constant and independent of the change in the mechanical state, the flux consists partly of a main flux ($\phi_O$) associated with the driving magnetizing force ($H_O$) having a definite direction and being of such a magnitude that the magnetic properties of the body depart from the region of irreversibility and partly of an alternating gradually vanishing flux ($\phi_v$) superposed upon the main flux, the alternating gradually vanishing flux must have such an initial magnitude that saturation is obtained in both directions of the alternating gradually vanishing flux ($\phi_v$), so that, a point on the anhysteretic curve of the body is reached when the alternating flux ($\phi_v$) has vanished, thereafter the disturbance generated through the change in the mechanical state is indicated or registered as a voltage, which is induced by the change in flux corresponding to the disturbance.

2. A device for measuring or detecting a change in the mechanical state in a body, comprising means for generating the flux in the body, characterized in that said means is arranged to form a magnetic circuit with at least a part of the body which circuit is essentially free from air gaps and has an average length (l) which is independent of the change in the mechanical state, means to drive a main flux ($\phi_O$) and a superposed alternating gradually vanishing flux ($\phi_v$) and a system of coils connected to a measuring or indicating equipment which is arranged to detect the change in the flux.

3. A device according to claim 2, characterized in that said generating means comprises a system of coils with yokes which together with the body forms the magnetic circuit and a current generator which is arranged to supply the system of coils with partly a direct current corresponding to the main flux and partly an alternating gradually vanishing current corresponding to alternating gradually vanishing flux.

4. Device according to claim 2, characterized in that said means comprises a system of permanent magnets for generating the main flux.

5. Device according to claim 3, characterized in that the yoke or yokes are slidably arranged on the body.

* * * * *